United States Patent
Min et al.

(10) Patent No.: US 9,176,038 B2
(45) Date of Patent: Nov. 3, 2015

(54) APPARATUS AND METHOD FOR PROCESSING BIOLOGICAL MATERIAL

(75) Inventors: Kyungyoon Min, Kildeer, IL (US); Thomas E. Dudar, Palatine, IL (US); James C. Laird, Grayslake, IL (US)

(73) Assignees: BAXALTA INCORPORATED, Bannockburn, IL (US); BAXALTA GMBH, Glattpark (Opfikon) (CH)

( * ) Notice: Subject to any disclaimer, the term of this patent is extended or adjusted under 35 U.S.C. 154(b) by 26 days.

(21) Appl. No.: 13/611,211

(22) Filed: Sep. 12, 2012

(65) Prior Publication Data

US 2013/0001157 A1 Jan. 3, 2013

Related U.S. Application Data

(62) Division of application No. 12/326,061, filed on Dec. 1, 2008, now Pat. No. 8,309,343.

(51) Int. Cl.
*B01L 3/00* (2006.01)
*B01D 21/00* (2006.01)
*B01D 21/26* (2006.01)
(Continued)

(52) U.S. Cl.
CPC ............ *G01N 1/4077* (2013.01); *B01L 3/5021* (2013.01); *B01L 3/5635* (2013.01); *C12M 47/02* (2013.01); *A61M 39/045* (2013.01); *A61M 39/26* (2013.01); *B01D 21/26* (2013.01); *B01D 21/262* (2013.01); *B01L 1/00* (2013.01); *B01L 3/502* (2013.01); *B01L 3/5027* (2013.01); *B01L 3/50273* (2013.01); *B01L 3/50825* (2013.01); *B01L 3/502738* (2013.01); *B01L 3/502753* (2013.01); *B01L 2200/025* (2013.01); *B01L 2200/026* (2013.01); *B01L 2200/0621* (2013.01); *B01L 2200/0647* (2013.01); *B01L 2200/10* (2013.01); *B01L 2300/044* (2013.01); *B01L 2300/046* (2013.01); *B01L 2300/049* (2013.01); *B01L 2400/0409* (2013.01); *B01L 2400/0478* (2013.01); *B01L 2400/0481* (2013.01); *B01L 2400/0633* (2013.01); *G01N 1/40* (2013.01); *G01N 15/042* (2013.01); *G01N 21/03* (2013.01); *G01N 21/07* (2013.01); *G01N 2001/4083* (2013.01); *G01N 2015/149* (2013.01); *G01N 2035/1058* (2013.01)

(58) Field of Classification Search
None
See application file for complete search history.

(56) References Cited

U.S. PATENT DOCUMENTS

| 2,539,082 A | 1/1951 | Hustinx |
| 3,713,778 A | 1/1973 | Karamian |

(Continued)

FOREIGN PATENT DOCUMENTS

| DE | 3924862 A1 | 1/1991 |
| EP | 0311011 A2 | 4/1989 |

(Continued)

OTHER PUBLICATIONS

PCT International Search Report and PCT Written Opinion of the International Searching Authority for PCT/US2009/064297 dated Mar. 22, 2010.

(Continued)

*Primary Examiner* — Jennifer Wecker
(74) *Attorney, Agent, or Firm* — Marshall, Gerstein & Borun LLP

(57) ABSTRACT

The application discloses an apparatus and method for processing biological material, including a suspension of cells.

16 Claims, 14 Drawing Sheets

(51) Int. Cl.
*C12M 1/00* (2006.01)
*G01N 1/40* (2006.01)
G01N 15/04 (2006.01)
G01N 21/07 (2006.01)
B01L 1/00 (2006.01)
G01N 15/14 (2006.01)
G01N 21/03 (2006.01)
G01N 35/10 (2006.01)
A61M 39/04 (2006.01)
A61M 39/26 (2006.01)

(56) References Cited

U.S. PATENT DOCUMENTS

| | | | |
|---|---|---|---|
| 3,750,645 A | 8/1973 | Bennett et al. | |
| 3,897,902 A | 8/1975 | Yanez | |
| 3,911,918 A | 10/1975 | Turner | |
| 3,914,985 A | 10/1975 | von Behrens | |
| 4,035,294 A | 7/1977 | Landers et al. | |
| 4,040,959 A | 8/1977 | Berman et al. | |
| 4,066,414 A | 1/1978 | Selby | |
| 4,268,393 A | 5/1981 | Persidsky et al. | |
| 4,344,560 A | 8/1982 | Iriguchi et al. | |
| 4,416,778 A | 11/1983 | Rogers | |
| 4,582,606 A | 4/1986 | McCarty | |
| 4,617,009 A | 10/1986 | Ohlin et al. | |
| 4,683,916 A | 8/1987 | Raines | |
| 4,772,273 A | 9/1988 | Alchas | |
| 4,811,866 A | 3/1989 | Golias | |
| 4,820,626 A | 4/1989 | Williams et al. | |
| 4,824,560 A | 4/1989 | Alspector | |
| 4,834,703 A | 5/1989 | Dubrul et al. | |
| 4,889,524 A | 12/1989 | Fell | |
| 4,975,186 A | 12/1990 | Wada et al. | |
| 4,981,654 A | 1/1991 | Kuntz et al. | |
| 5,019,512 A | 5/1991 | Varecka et al. | |
| 5,030,215 A | 7/1991 | Morse et al. | |
| 5,035,708 A | 7/1991 | Alchas et al. | |
| 5,079,160 A | 1/1992 | Lacy et al. | |
| 5,103,821 A | 4/1992 | King | |
| 5,131,907 A | 7/1992 | Williams et al. | |
| 5,188,620 A | 2/1993 | Jepson et al. | |
| 5,194,145 A | 3/1993 | Schoendorfer | |
| 5,230,693 A | 7/1993 | Williams et al. | |
| 5,271,852 A * | 12/1993 | Luoma, II | 210/789 |
| 5,312,380 A | 5/1994 | Alchas et al. | |
| 5,316,681 A | 5/1994 | Serres | |
| 5,364,386 A | 11/1994 | Fukuoka et al. | |
| 5,372,945 A | 12/1994 | Alchas et al. | |
| 5,409,833 A | 4/1995 | Hu et al. | |
| 5,441,539 A | 8/1995 | Alchas et al. | |
| 5,462,716 A | 10/1995 | Holm | |
| 5,578,059 A | 11/1996 | Patzer | |
| 5,628,781 A | 5/1997 | Williams et al. | |
| 5,634,879 A | 6/1997 | Mueller-Glauser et al. | |
| 5,679,565 A | 10/1997 | Mullen et al. | |
| 5,707,876 A | 1/1998 | Levine et al. | |
| 5,770,069 A | 6/1998 | Meryman | |
| 5,786,207 A | 7/1998 | Katz et al. | |
| 5,804,366 A | 9/1998 | Hu et al. | |
| 5,824,272 A | 10/1998 | Uchida | |
| 5,837,444 A | 11/1998 | Shah | |
| 5,888,409 A | 3/1999 | Morsiani et al. | |
| 5,919,703 A | 7/1999 | Mullen | |
| 5,957,898 A | 9/1999 | Jepson et al. | |
| 5,957,972 A | 9/1999 | Williams et al. | |
| 5,968,356 A | 10/1999 | Morsiani et al. | |
| 6,001,643 A | 12/1999 | Spaulding | |
| 6,039,302 A | 3/2000 | Cote et al. | |
| 6,090,572 A | 7/2000 | Crosby | |
| 6,123,655 A | 9/2000 | Fell | |
| 6,123,696 A | 9/2000 | Coelho et al. | |
| 6,177,009 B1 | 1/2001 | Sieber et al. | |
| 6,207,445 B1 | 3/2001 | Crosby | |
| 6,221,315 B1 | 4/2001 | Giesler et al. | |
| 6,238,922 B1 | 5/2001 | Uchida | |
| 6,261,282 B1 | 7/2001 | Jepson et al. | |
| 6,267,927 B1 | 7/2001 | Pomar Longedo et al. | |
| 6,280,400 B1 | 8/2001 | Niermann | |
| 6,309,606 B1 | 10/2001 | Sitar | |
| 6,316,247 B1 | 11/2001 | Katz et al. | |
| 6,325,750 B1 | 12/2001 | Jorgensen et al. | |
| 6,358,474 B1 | 3/2002 | Dobler et al. | |
| 6,398,719 B1 | 6/2002 | Kaneko et al. | |
| 6,398,972 B1 | 6/2002 | Blasetti et al. | |
| 6,401,552 B1 * | 6/2002 | Elkins | 73/863 |
| 6,448,076 B2 | 9/2002 | Dennis et al. | |
| 6,491,819 B2 | 12/2002 | Prince et al. | |
| 6,497,821 B1 | 12/2002 | Bellamy et al. | |
| 6,589,153 B2 | 7/2003 | Dolochek et al. | |
| 6,596,180 B2 | 7/2003 | Baugh et al. | |
| 6,602,718 B1 | 8/2003 | Augello et al. | |
| 6,605,076 B1 | 8/2003 | Jepson et al. | |
| 6,610,002 B2 | 8/2003 | Dolochek | |
| 6,617,170 B2 | 9/2003 | Augello et al. | |
| 6,623,959 B2 | 9/2003 | Harris | |
| 6,777,231 B1 | 8/2004 | Katz et al. | |
| 6,780,333 B1 | 8/2004 | Brown et al. | |
| 6,833,270 B2 | 12/2004 | Poo et al. | |
| RE38,730 E | 4/2005 | Wells et al. | |
| 6,890,728 B2 | 5/2005 | Dolochek et al. | |
| 6,905,612 B2 | 6/2005 | Dorian et al. | |
| RE38,757 E | 7/2005 | Wells et al. | |
| 7,045,349 B2 | 5/2006 | Benedict et al. | |
| 7,118,676 B2 | 10/2006 | Mueth et al. | |
| 7,188,994 B2 | 3/2007 | Poo et al. | |
| 7,241,293 B2 | 7/2007 | Davison | |
| 7,250,036 B2 | 7/2007 | Alchas | |
| 7,306,740 B2 | 12/2007 | Freund | |
| 7,341,062 B2 | 3/2008 | Chachques et al. | |
| 7,390,484 B2 | 6/2008 | Fraser et al. | |
| 7,429,488 B2 | 9/2008 | Fraser et al. | |
| 7,435,586 B2 | 10/2008 | Bartlett et al. | |
| 7,501,115 B2 | 3/2009 | Fraser et al. | |
| 7,520,402 B2 | 4/2009 | Ellsworth et al. | |
| 7,597,277 B2 | 10/2009 | Kawakami et al. | |
| 2001/0009757 A1 | 7/2001 | Bischof et al. | |
| 2002/0031827 A1 | 3/2002 | Kanno et al. | |
| 2002/0077687 A1 | 6/2002 | Ahn | |
| 2002/0146817 A1 | 10/2002 | Cannon et al. | |
| 2002/0147099 A1 | 10/2002 | Dolochek | |
| 2003/0029790 A1 * | 2/2003 | Templeton | 210/512.1 |
| 2003/0050591 A1 | 3/2003 | McHale | |
| 2003/0082152 A1 | 5/2003 | Hedrick et al. | |
| 2004/0010231 A1 | 1/2004 | Leonhardt et al. | |
| 2004/0039188 A1 | 2/2004 | Gautsch et al. | |
| 2004/0115689 A1 | 6/2004 | Augello et al. | |
| 2004/0167004 A1 | 8/2004 | Jorgensen et al. | |
| 2004/0209755 A1 | 10/2004 | Moore et al. | |
| 2004/0248077 A1 | 12/2004 | Rodriguez Rilo et al. | |
| 2005/0014273 A1 | 1/2005 | Dahm et al. | |
| 2005/0025755 A1 | 2/2005 | Hedrick et al. | |
| 2005/0026275 A1 | 2/2005 | Bahoric | |
| 2005/0058632 A1 | 3/2005 | Hedrick et al. | |
| 2005/0076396 A1 | 4/2005 | Katz et al. | |
| 2005/0084961 A1 | 4/2005 | Hedrick et al. | |
| 2005/0125049 A1 | 6/2005 | Brown et al. | |
| 2005/0153441 A1 | 7/2005 | Hedrick et al. | |
| 2005/0153442 A1 | 7/2005 | Katz et al. | |
| 2005/0171578 A1 | 8/2005 | Leonhardt | |
| 2005/0186671 A1 | 8/2005 | Cannon et al. | |
| 2005/0250202 A1 | 11/2005 | March et al. | |
| 2005/0260175 A1 | 11/2005 | Hedrick et al. | |
| 2006/0045872 A1 | 3/2006 | Miguel | |
| 2006/0074394 A1 * | 4/2006 | Beretta et al. | 604/414 |
| 2006/0134597 A1 | 6/2006 | Chang | |
| 2006/0134781 A1 | 6/2006 | Yang et al. | |
| 2006/0160221 A1 | 7/2006 | Siebenkotten et al. | |
| 2006/0175268 A1 | 8/2006 | Dorian et al. | |
| 2006/0258004 A1 | 11/2006 | Kosnik et al. | |
| 2006/0278588 A1 * | 12/2006 | Woodell-May | 210/787 |
| 2006/0286669 A1 | 12/2006 | Song | |
| 2007/0075016 A1 | 4/2007 | Leach | |

(56) References Cited

U.S. PATENT DOCUMENTS

| | | |
|---|---|---|
| 2007/0092876 A1 | 4/2007 | Xu |
| 2007/0110729 A1 | 5/2007 | Kang et al. |
| 2007/0131612 A1 | 6/2007 | Duffy et al. |
| 2007/0148756 A1 | 6/2007 | Bullen |
| 2007/0154465 A1 | 7/2007 | Kharazi et al. |
| 2007/0160582 A1* | 7/2007 | Madlambayan et al. .... 424/93.7 |
| 2007/0208321 A1 | 9/2007 | Leach et al. |
| 2007/0218553 A1 | 9/2007 | Rodriguez Rilo et al. |
| 2007/0243574 A1 | 10/2007 | Williams et al. |
| 2007/0267444 A1* | 11/2007 | de Buzzaccarini et al. .... 222/179.5 |
| 2007/0274960 A1 | 11/2007 | Harman et al. |
| 2007/0286669 A1 | 12/2007 | Nuebel et al. |
| 2008/0014181 A1 | 1/2008 | Ariff et al. |
| 2008/0020446 A1 | 1/2008 | Jia |
| 2008/0032398 A1 | 2/2008 | Cannon et al. |
| 2008/0058763 A1 | 3/2008 | Boland |
| 2008/0145926 A1 | 6/2008 | Kugelmann et al. |
| 2008/0160085 A1 | 7/2008 | Boland et al. |
| 2008/0171951 A1 | 7/2008 | Fell |
| 2008/0217265 A1 | 9/2008 | Leach et al. |
| 2008/0226604 A9 | 9/2008 | Kellar et al. |
| 2008/0283474 A1* | 11/2008 | Leach et al. ................. 210/789 |
| 2008/0286379 A1* | 11/2008 | Wehling et al. ............... 424/530 |
| 2009/0084737 A1 | 4/2009 | Bachur, Jr. |
| 2009/0304644 A1 | 12/2009 | Hedrick et al. |
| 2010/0285588 A1* | 11/2010 | Stubbers et al. .............. 435/379 |

FOREIGN PATENT DOCUMENTS

| | | |
|---|---|---|
| EP | 0512769 A2 | 11/1992 |
| EP | 0723009 A1 | 7/1996 |
| EP | 0749771 A2 | 12/1996 |
| EP | 0779077 A1 | 6/1997 |
| EP | 0792662 A2 | 9/1997 |
| EP | 1005909 A2 | 6/2000 |
| EP | 1005910 A2 | 6/2000 |
| EP | 1006360 A2 | 6/2000 |
| EP | 1014088 A2 | 6/2000 |
| EP | 1106253 A2 | 6/2001 |
| EP | 1447072 A1 | 8/2004 |
| EP | 1459807 A1 | 9/2004 |
| EP | 1007631 B2 | 10/2005 |
| EP | 1848472 A1 | 10/2007 |
| EP | 1862535 A1 | 12/2007 |
| EP | 1869165 A1 | 12/2007 |
| EP | 2046349 A1 | 4/2009 |
| GB | 1 189 775 | 4/1970 |
| JP | 06098754 | 4/1994 |
| JP | 2002-519649 | 7/2002 |
| JP | 03235543 | 8/2003 |
| JP | 2005-505294 | 2/2005 |
| JP | 05218376 | 8/2005 |
| JP | 05287479 | 10/2005 |
| JP | 08271971 | 11/2008 |
| JP | 08278821 | 11/2008 |
| JP | 08278822 | 11/2008 |
| WO | WO9400169 A1 | 1/1994 |
| WO | WO9427698 A2 | 12/1994 |
| WO | WO9517938 A1 | 7/1995 |
| WO | WO9522391 A1 | 8/1995 |
| WO | WO 96/06679 | 3/1996 |
| WO | WO9607097 A1 | 3/1996 |
| WO | WO9902958 A1 | 1/1999 |
| WO | WO03009889 A1 | 2/2003 |
| WO | WO 03/033215 | 4/2003 |
| WO | WO03037476 A1 | 5/2003 |
| WO | WO2004027014 A1 | 4/2004 |
| WO | WO2004106485 A1 | 12/2004 |
| WO | WO2005030361 A1 | 4/2005 |
| WO | WO2005087921 A1 | 9/2005 |
| WO | WO2006100651 A1 | 9/2006 |
| WO | WO2007000966 A1 | 1/2007 |
| WO | WO2007079149 A2 | 7/2007 |
| WO | WO2007080410 A1 | 7/2007 |
| WO | WO 2007/109639 | 9/2007 |
| WO | WO2008042174 A3 | 4/2008 |
| WO | WO2009046058 A1 | 4/2009 |

OTHER PUBLICATIONS

PCT International Preliminary Report on Patentability for PCT/US2009/064297 dated Feb. 16, 2011.
European Office Action, European patent application No. 09764357.1, dated Mar. 31, 2015.

* cited by examiner

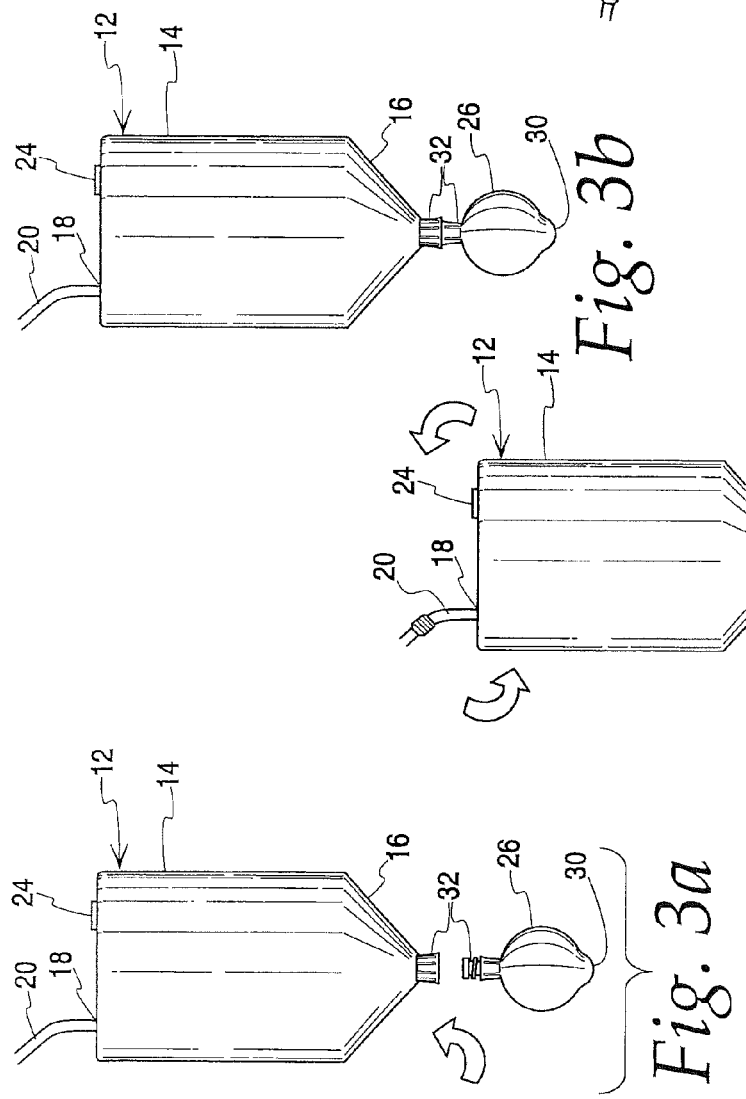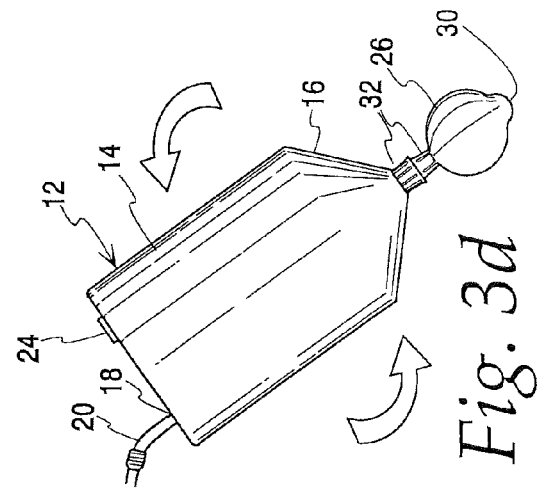

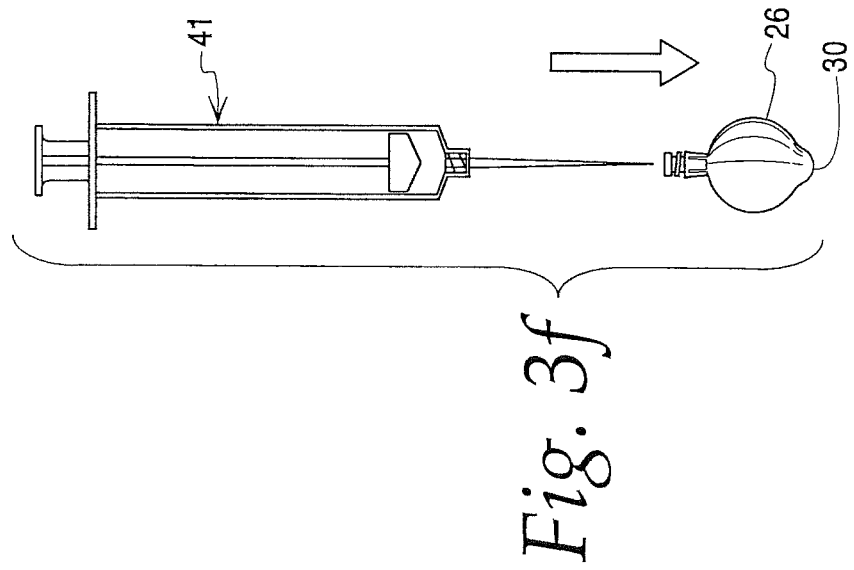
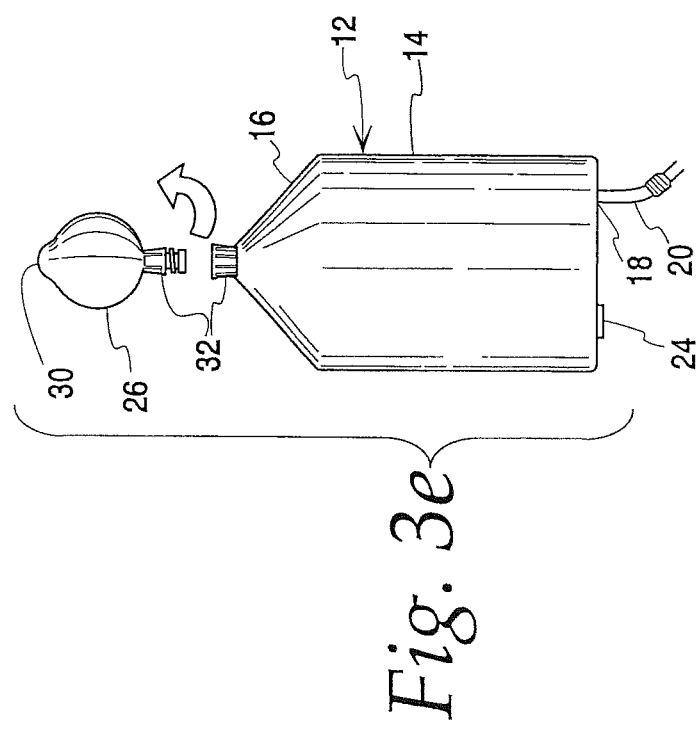
Fig. 3f
Fig. 3e

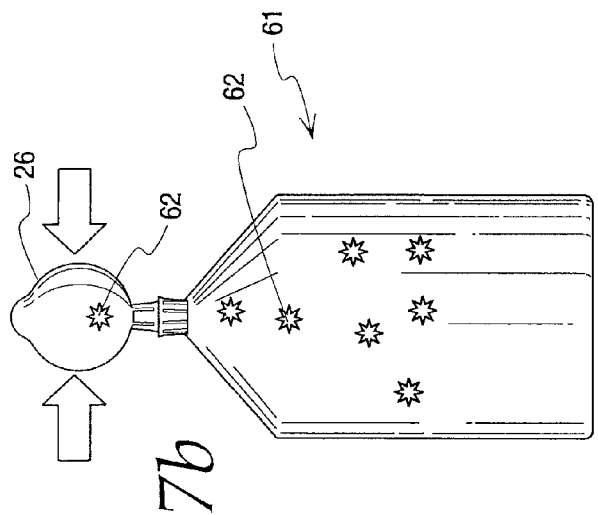
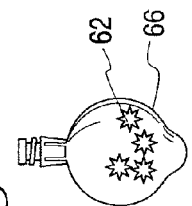
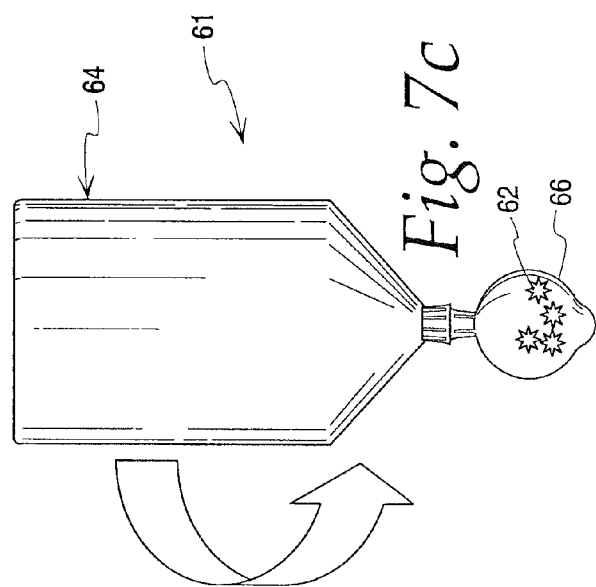
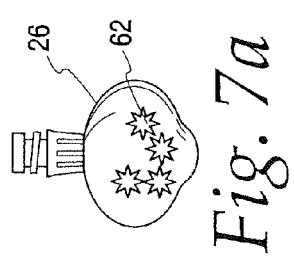

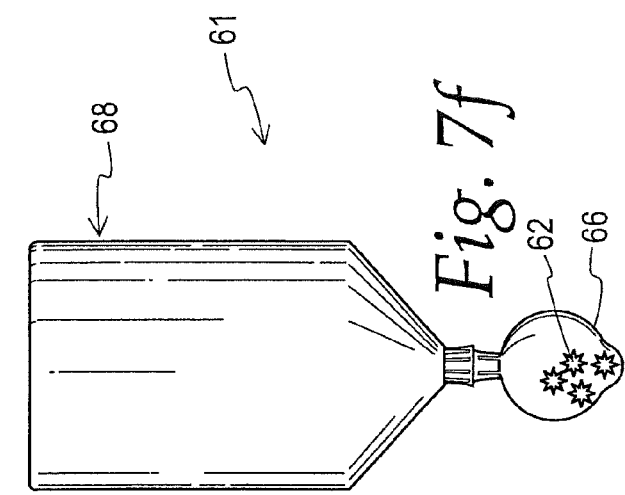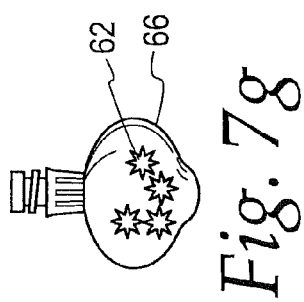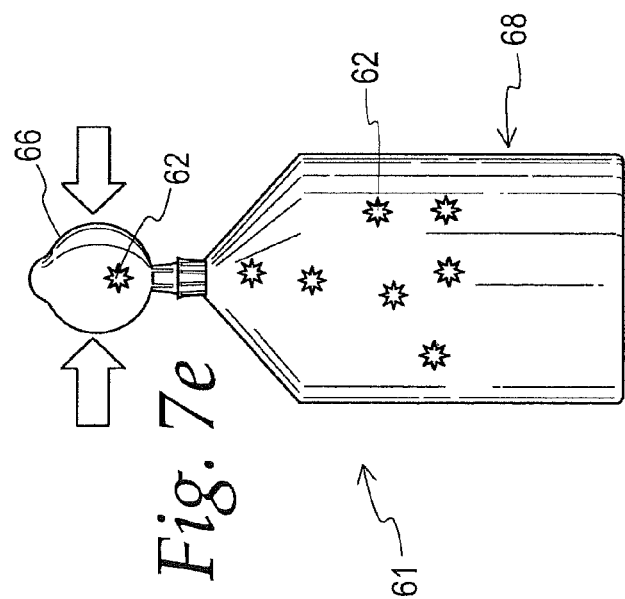

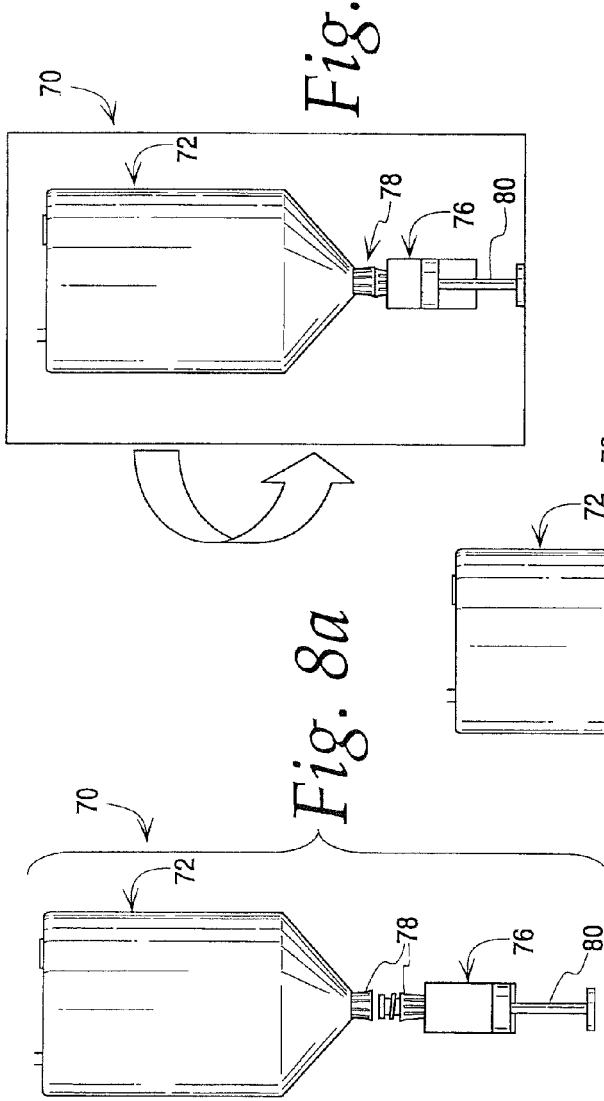
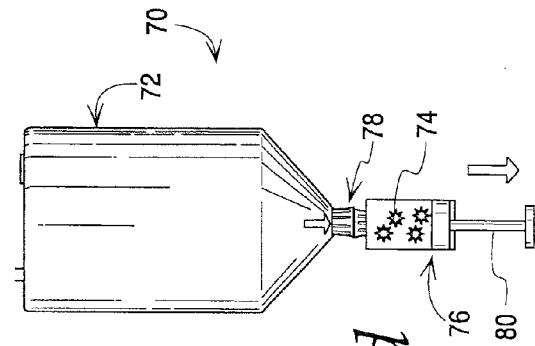
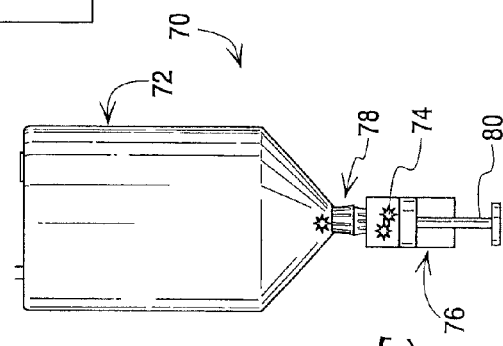
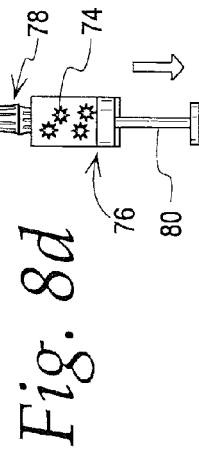

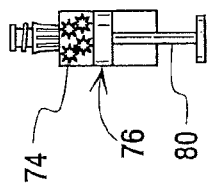
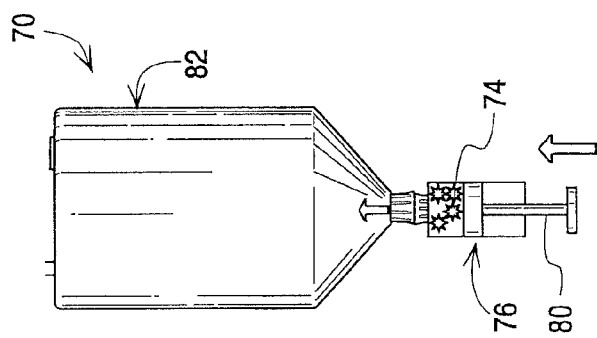
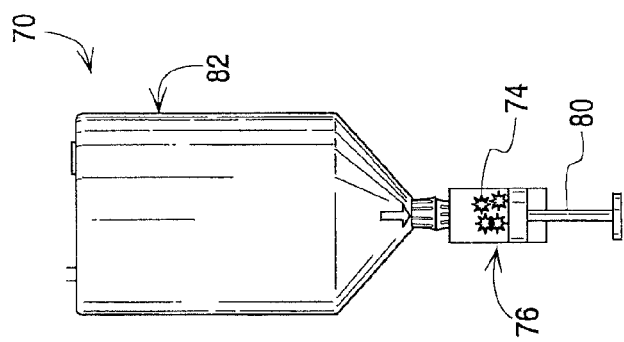
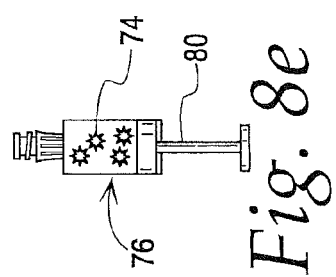

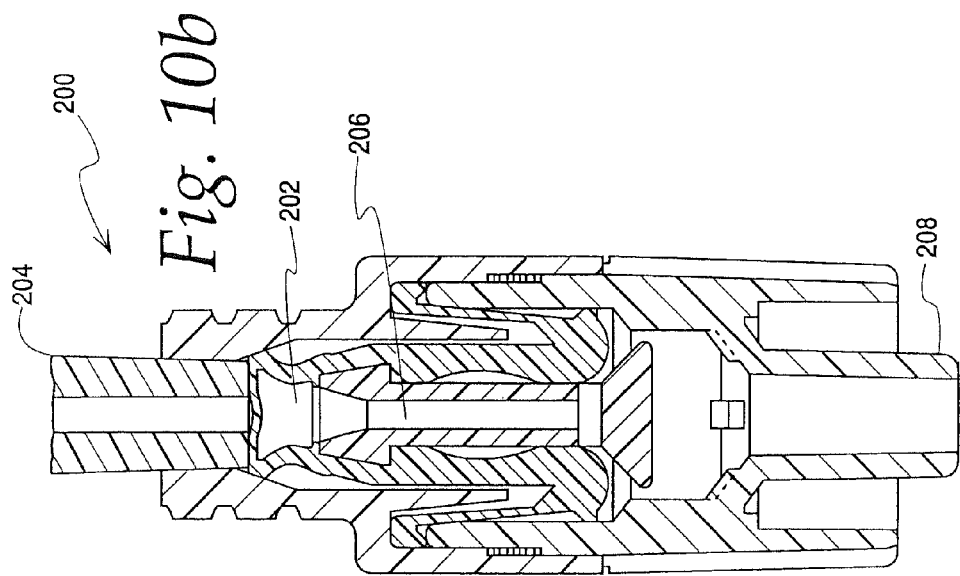
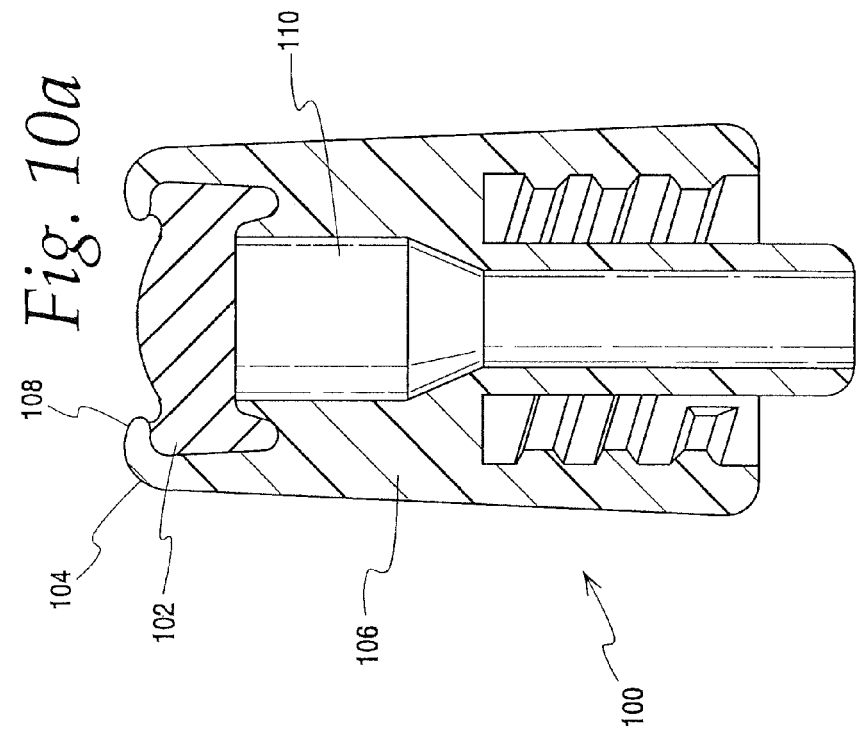

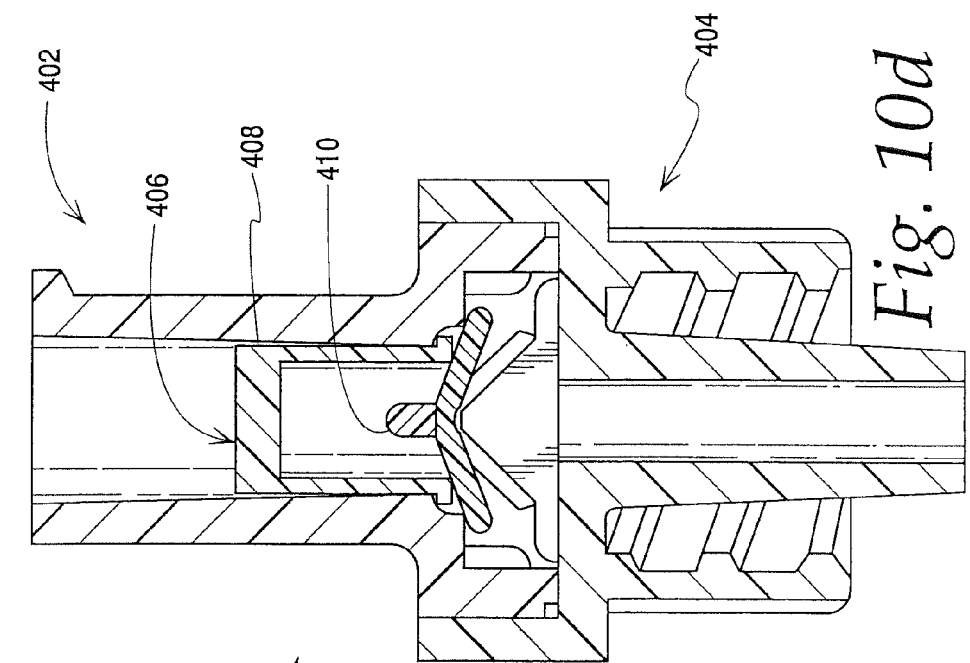
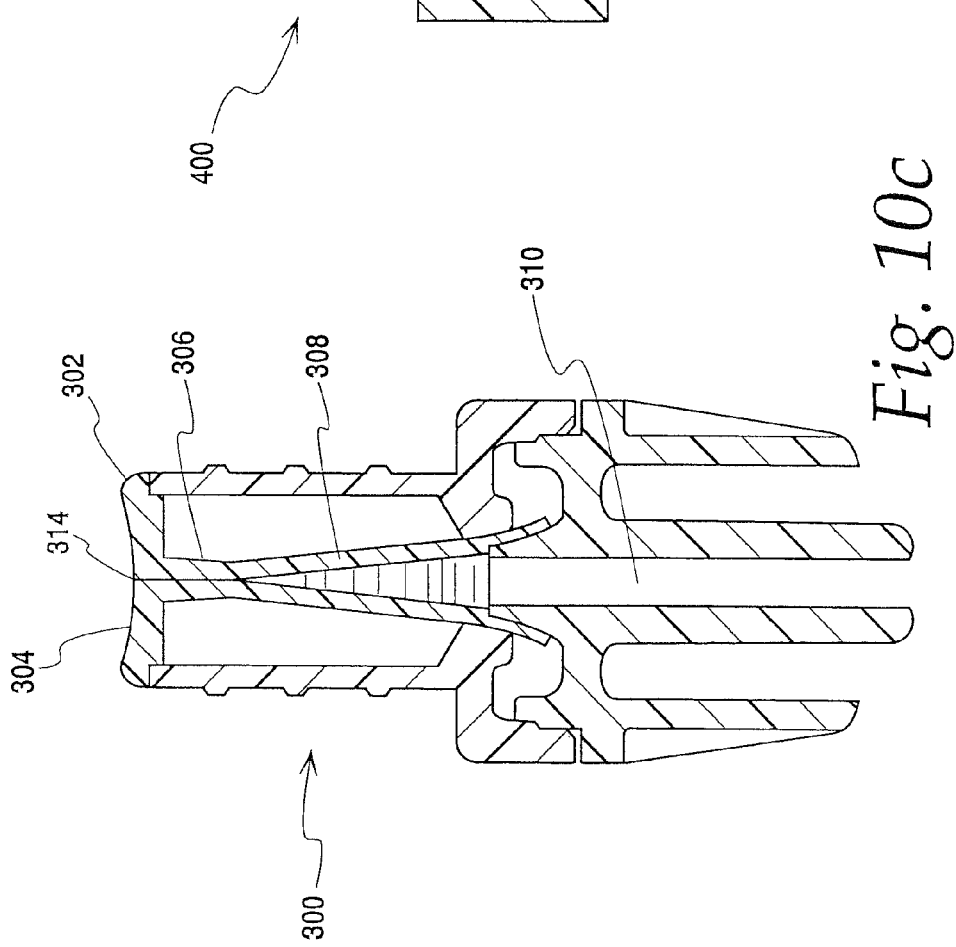

APPARATUS AND METHOD FOR PROCESSING BIOLOGICAL MATERIAL

This application is a divisional application of U.S. application Ser. No. 12/326,061, filed Dec. 1, 2008 now U.S. Pat. No. 8,309,343, which is hereby incorporated by reference.

TECHNICAL FIELD

The present subject matter generally relates to an apparatus and method for processing biological material to concentrate and wash a biological component in the material.

BACKGROUND

Biological materials, such as cells, are used in numerous therapeutic, diagnostic and research applications. For example, stem cells may be administered to patients to obtain a desired therapeutic effect such as regeneration of tissue in vivo. In other situations, biological materials including cells may be administered for grafts, transplants, or other procedures.

To provide an effective preparation of the biological material, having sufficient concentration that may be administered to a patient or that may be useful for diagnostic and research purposes, it often is necessary to perform numerous and lengthy manipulations involving the material. For example, stem cells often are first separated and isolated from a tissue from which they are derived, such as muscle, blood or adipose (fat) tissue. The cells of such a composition then may have to be subjected to multiple rounds of purification, washing or other treatments before they can be introduced, such as by injection, into a patient. These procedures may require sequential transfer of the cells to different containers. They also may require further manipulations, such as to promote sedimentation. Each procedure preferably is performed aseptically or in a closed sterile system to limit or avoid the potential introduction of contaminating material or organisms into the composition. Alternatively, even if the cells will not be administered to a patient but, instead cultured in vitro, for example, they still may require extensive washing and concentration preferably in aseptic conditions.

Also, to be suitable for administration to a patient, it may be preferable for a preparation of biological material to be highly concentrated. This may permit a relatively small volume to be administered. For example, stem cell preparations of about $1 \times 10^8$ cells or more generally may be concentrated into a volume of less than five (5) mls for injection into a patient.

Although much work has been done in the field of tissue processing, there continues to be a need for advances in the field of processing biological material including in the areas of washing and concentrating material for subsequent therapeutic, diagnostic, research or other applications.

SUMMARY

In one example, the subject matter of this application is directed to a sedimentation assembly for concentrating cells in a suspension. The sedimentation assembly includes a first chamber for receiving the suspension including a cell population. The first chamber has a cell concentration zone for receiving a concentrated population of the cells upon application of a sedimentation force upon the chamber. The assembly also includes a second chamber that is adapted to be removably placed in fluid communication with a fluid destination or source, including the concentration zone of the first chamber. The first and second chambers as a unit are placeable in a sedimentation force field with the first and second chambers in fluid communication for flowing a portion of the suspension including a cell population into the second chamber. The chambers are preferably physically separable so that fluid communication is effected physically by joining the chambers or broken by physically separating the chambers.

In another example, the disclosed subject matter is directed to a sedimentation assembly for washing and concentrating a cell population in a suspension. The sedimentation assembly includes a first chamber for receiving a suspension including a cell population. The sedimentation assembly also includes a second chamber, adapted to be removably placed in fluid communication with a fluid destination or source, including the first chamber. The first and second chambers are placeable as a unit in a sedimentation force field with the first and second chambers in fluid communication, such that when the unit is subjected to the sedimentation force field at least a portion of the suspension flows from the first chamber to the second chamber, thereby forming a concentrated cell suspension in the second chamber.

The disclosure also is directed to methods of concentrating cells in a suspension. In one example, a method of concentrating cells in a suspension includes collecting a suspension including a cell population within a first chamber. The cell population is sedimented to obtain a concentrated cell suspension within the first chamber and the concentrated cell suspension is flowed into a second chamber under a sedimentation force field.

In a further example, a method of concentrating and washing cells in a suspension is disclosed. The method includes collecting a suspension including a cell population within a first chamber and sedimenting the cell population to obtain a concentrated cell suspension within the first chamber. The concentrated cell suspension is flowed into a second chamber under a sedimentation force field. The second chamber is detached from the first chamber and the concentrated cell suspension is flowed into a further fluid destination or source. The further fluid destination or source is placeable together with the second chamber in a sedimentation force field.

In a further example, an apparatus for reconstituting, washing or treating a cell preparation is described. The apparatus has a first chamber with at least one port. The apparatus also includes a second chamber that has at least one port and that is adapted to be repeatedly and removably placed in fluid communication with a fluid destination or source, such as the first chamber. At least one port of the first chamber has a resealable valve and at least one port of the second chamber has a member for opening the valve.

A method for reconstituting, washing or treating a cell preparation is also disclosed. The method includes placing a cell preparation within a first chamber and flowing the cell preparation from the first chamber into a second chamber which is adapted to be repeatedly and removably connected to and placed in fluid communication with the first chamber. One of the first and second chambers has a port having an automatically resealable valve and the other of the first and second chambers has a port having a member adapted to automatically open the valve when the chambers are connected. The second chamber is then disconnected from the first chamber and the valve automatically closed.

BRIEF DESCRIPTION OF THE DRAWINGS

FIG. 1a is an enlarged cross-sectional view of one example of a coupling between the first and second chambers of FIG. 1, with the chambers shown in a separated position;

FIGS. 3a-3f show one example of a method of using the sedimentation assembly of FIG. 1 according to the disclosure;

FIGS. 7a-7g show an example of a method of using the sedimentation assembly of FIG. 1 according to the disclosure;

FIGS. 8a-8h show an example of a method of use of another sedimentation assembly according to the disclosure, where one chamber includes a plunger;

FIGS. 10a-d are cross-sectional views of further examples of valves and connectors that may be used with an apparatus disclosed herein.

DETAILED DESCRIPTION

While detailed examples are disclosed herein, it is to be understood that these disclosed examples are merely exemplary, and various aspects and features described herein may have utility alone or in combination with other features or aspects in a manner other than explicitly shown but would be apparent to a person of ordinary skill in the art.

The subject matter of the present application is directed generally to an apparatus and method for processing biological material. In one example, the apparatus is a sedimentation assembly that may be used to concentrate biological material. In other preferred examples, the sedimentation assembly may be used to reconstitute, wash and/or otherwise treat the material with desired reagents and solutions. For example, the apparatus may be used to wash or treat cell preparations with selected buffers. In other examples, the apparatus may be used to treat a cell preparation with reagents such as serum, antibodies or growth factors. In further examples, the apparatus may be used to prepare cells for freezing and storage and may be used reconstitute a cell preparation that had been frozen and which may be required to be transferred to culture media.

In other preferred examples, the apparatus may be used to reconstitute, wash or otherwise treat a preparation of cells without necessarily sedimenting the cells. For example, the apparatus may be used to transfer a thawed cell preparation to tissue culture media so that the cells may be cultured.

Figure 1:
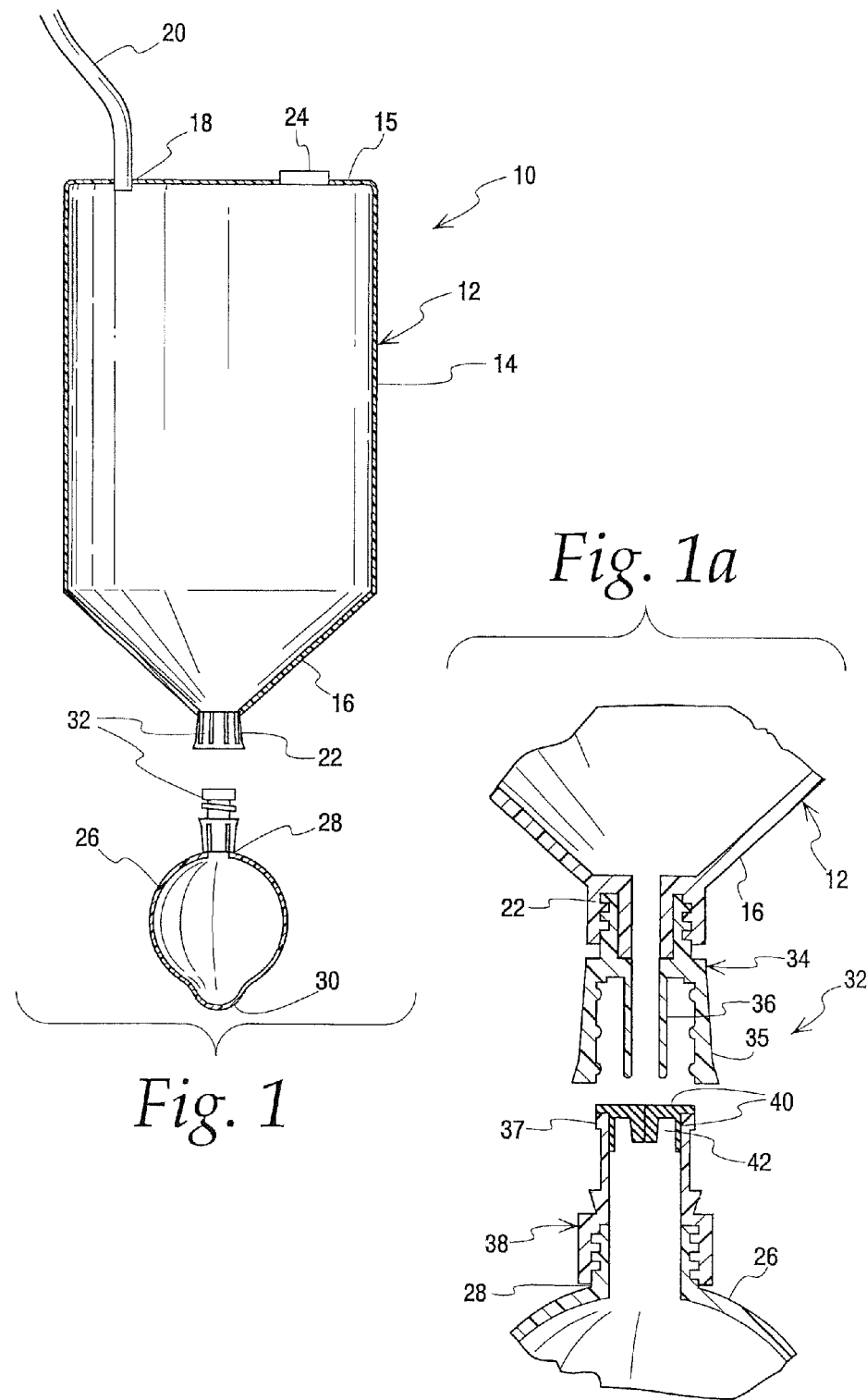
FIG. 1 is a partial cross-sectional view of one example of a sedimentation assembly according to the disclosure where first and second chambers are shown in a separated position and out of fluid communication.
Figure 2:
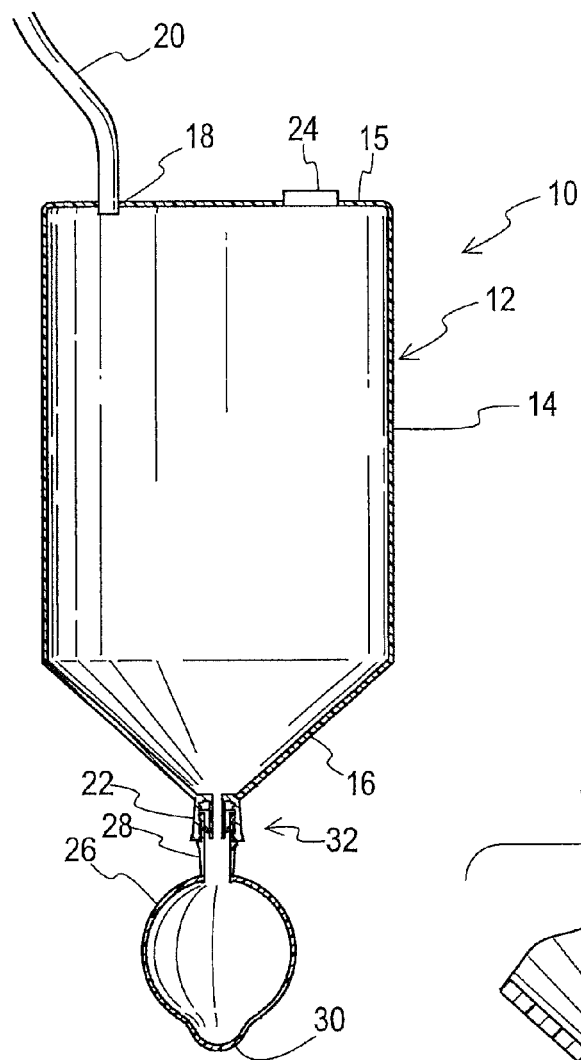
FIG. 2 is a partial cross-sectional view of the of sedimentation assembly of FIG. 1 with the first and second chambers shown in a connected position in fluid communication.

Turning to the accompanying drawings, FIG. 1 illustrates a sedimentation assembly generally at 10 that may be used in concentrating biological material, such as cells, from tissue. The sedimentation assembly includes a first chamber 12 that may receive biological material, such as a suspension of cells. The sedimentation assembly 10 also includes a second chamber 26 that may be placed in fluid communication with the first chamber 12, for example, as seen in FIG. 2. That is, the first chamber 12 and second chamber 26 may be readily coupled together or connected to form a sedimentation assembly 10 as a stable, integrated unit. The chambers 12, 26 then may be separated and then reconnected, if necessary, so that fluid communication between the chambers may be repeatedly established, removed and re-established. For example, FIG. 1 shows the sedimentation assembly 10 with the first and second chambers 12, 26 separated—and thus fluid communication has not yet been established or has been removed. FIG. 2 shows the assembly 10 with the two chambers connected or having been reconnected and placed in fluid communication. As shown in FIGS. 1 and 2, a coupling 32 may be used to facilitate the connection, separation and reconnection of the two chambers.

In one example, the first chamber 12 is substantially rigid and the second chamber 26 may have the same or different degree of rigidity. The chambers, for example, may be generally be more rigid than bags commonly used in blood processing procedures, but may retain a degree of flexibility. Thus, in some examples, the chambers may be sufficiently pliable such that they may be manipulated by the application of no more than an average manual force. The chambers 12, 26 may be formed, at least in part, of substantially rigid transparent plastics such that the contents may be viewed during processing. Of course, the first and second chambers need not necessarily be made of the same materials or have the same degree of rigidity. In one preferred example, at least part of the second chamber 26 may be less rigid than the first chamber 12, thereby permitting the volume of the second chamber to be manipulated or expelled by the application of force to the wall of the second chamber or by a change in pressure of the chamber.

The sedimentation assembly also is preferably disposable, and may be made from polyethylene, polypropylene or other materials that are suitable for use with biological material and that may be easily sterilized before use, or otherwise provided in a sterile form. Although typically not believed to be necessary, the chamber surfaces may be treated or coated with materials such as serum, albumin, polycations, polyanions, or other materials, as desired, using methods known in the art, to increase or decrease the adherence or affinity of selected biological material to the walls of the first and second chambers, or for other purposes.

The volumes of the first and second chambers 12, 26 may be selected depending on particular requirements. In one example, such as shown in FIG. 1, the second chamber 26 has a smaller volume than the first chamber 12. This example may be used, for example, when the suspension of cells is to be concentrated into a smaller volume for administration to a patient or for further processing. The chambers 12, 26 also may assume numerous shapes, as desired. For example, as described further herein, one or both chambers may be in the form of a syringe with a moveable plunger therein.

In the example shown in FIG. 1, the first chamber 12 has an upper wall portion 14 which is cylindrical. The upper wall portion 14 of the first chamber 12 is closed at an upper end by a wall or base 15 and is joined at a lower end to a conical or tapered portion, forming a concentration zone or area 16 within the first chamber 12, proximate its lower end. As shown in FIG. 1, an inlet tubing 20 may be attached to the first chamber 12 via an aperture 18 in the base 15. The inlet tubing 20 may be used to introduce biological material including a suspension of cells into the first chamber 12. The first chamber 12 also has an outlet 22 adjacent the lower end of the concentration zone 16. The first chamber 12 further includes a vent 24 in the base 15 to permit venting of air as may be required when fluid is being added to or removed from the first chamber 12.

In the example shown in FIGS. 1 and 2, the second chamber 26 is shown as having a substantially rigid spherical shape with a port 28 to permit the introduction and/or removal of fluid. Of course, the second chamber 26 may be constructed to be more or less flexible and to have a different shape, as desired. In this example, the second chamber 26 also includes a lower pocket or region 30 opposite the port 28. The pocket 30 provides a space or zone where cells can accumulate during sedimentation, and may facilitate later removal of a fluid from the second chamber 26 with less disruption to the cells collected in the pocket 30. Of course, the sedimented cells may be suspended within the second chamber and used directly as a final suspension for a desired purpose such as injection into a patient without further processing.

As noted above, in FIG. 1, the second chamber 26 is shown as physically separated from the first chamber 12. Therefore, the second chamber 26 has not yet established or has been removed from fluid communication with the first chamber 12. FIG. 2 shows the second chamber 26 as connected to the first chamber 12, so that the second chamber 26 is placed in fluid communication with the first chamber 12.

Figure 2A:
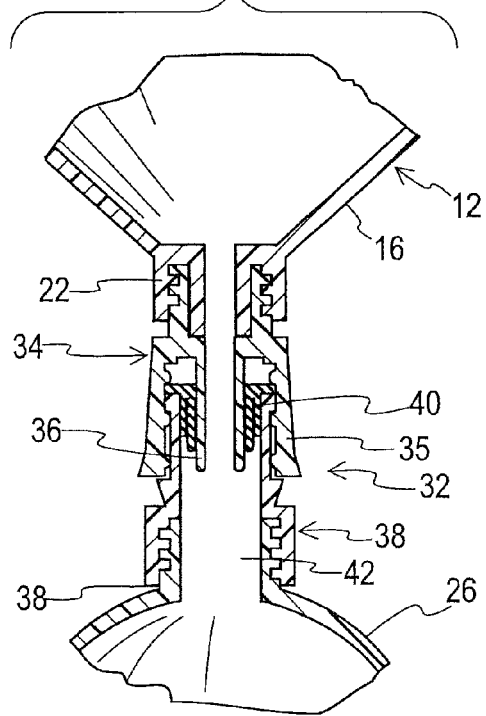
FIG. 2a is an enlarged cross-sectional view of the example of a coupling between the first and second chambers of FIG. 2, with the chambers shown in a connected position.

As shown in FIGS. 1 and 2, a separable coupling 32 may be utilized to facilitate the connection, separation and reconnection of the first chamber 12 and second chamber 26. FIGS. 1a and 2a show cross-sectional, enlarged views of an example coupling 32. FIG. 1a shows an arrangement of the coupling when the chambers 12, 26 are not connected and not in fluid communication with each other. FIG. 2a shows an arrangement when the chambers 12, 26 are connected and fluid communication between the chambers may have been established.

As shown in FIGS. 1a and 2a, the illustrated coupling 32 includes two mating elements. A first mating connector or element 34 of the coupling 32 is shown as being externally threaded at its upper end, and engaged with the first chamber 12 via complementary threads in the outlet 22. It will be appreciated that the first mating element 34 may be constructed in other ways to engage the first chamber 12 or may be molded with or otherwise connected to the first chamber 12. The first element 34 shown in FIGS. 1a and 2a also includes an outer collar 35 that is internally threaded, a blunt cannula 36, located within the collar.

A second mating connector or element 38 of the coupling 32 may be threaded, molded or otherwise connected to the second chamber 26 at its port 28. In the example illustrated in FIG. 1a, the second mating element 38 is shown with internal threads at its lower end that engage complementary external threads extending from the port 28 at the top of the second chamber 26. The second mating element 38 also includes at its upper end an external thread or flange 37 for mating with the internally threaded collar 35 of the first mating element 34.

In this illustrated example, the second mating element 38 of the coupling 32 further includes a flexible pre-slit, re-sealable septum valve 40. As seen in FIG. 1a, the septum valve 40 is biased towards a closed position. Therefore, the septum valve 40 automatically closes and seals the second chamber 26 from the environment when the first and second chambers 12, 26 are separated. As seen in FIG. 2a, the septum valve 40 also automatically seals against the cannula 36 when the chambers 12, 26 are connected.

The disclosed apparatus is not limited to a particular connector or valve construction shown. For example, the above elements may be otherwise constructed or reversed in their placement, if desired. It also will be appreciated that other examples may include valves on both chambers, as desired.

To join the two chambers 12, 26 and place them in fluid communication, the first and second mating elements 34, 38 of the coupling 32 are connected together. This causes the cannula 36 to pass through the re-sealable septum valve 40, as indicated in FIG. 2a. In this arrangement, the connector provides a closed passageway or channel 42 in the sedimentation assembly 10 that is sealed from the environment. In this regard, the septum valve is preferably elastically stretched about the penetrating member. In this example with the first and second chambers 12, 26 connected as a unit, fluid including cells i.e a cell suspension (or liquid alone), may flow in either direction (first chamber 12 to second chamber 26 or second chamber 26 to first chamber 12) depending on the direction and magnitude of forces applied to the sedimentation assembly 10. To remove the fluid communication between the chambers 12, 26, the cannula 36 is withdrawn from the septum valve 40, which automatically re-seals instantaneously.

FIGS. 3a-3f illustrates generally a method of use of a sedimentation assembly 10. As shown in FIGS. 3a and 3b, the first chamber 12, which has received a suspension of cells, may be connected to a second chamber 26 and fluid communication between the chambers may be established. A coupling 32 may be used to facilitate the connection of the two chambers, creating a sedimentation assembly 10 in the form of an integrated unit, with the chambers 12, 26 rigidly connected together by the coupling 32, as seen in FIG. 3b.

The sedimentation assembly 10 may be placed in a sedimentation force field, such as a centrifugal force field, although a simple gravitational force field, i.e. normal gravitational force, may be sufficient to promote sedimentation in certain circumstances. The sedimentation force field, such as developed by centrifugation in FIG. 3c, should be sufficient to cause desired cells of the suspension to become concentrated in the concentration zone 16 of the first chamber 12 and, optionally, to flow from the first chamber 12 to the second chamber 26.

After the second chamber 26 receives a quantity of the desired suspension of cells, the second chamber 26 may be separated from the first chamber 12, as illustrated in FIGS. 3d and 3e. Thus, the sedimentation assembly 10 may be inverted, as shown in FIG. 3d, to reduce potential spillage as the cannula 36 is removed from the septum valve 40. The second chamber 26 then may be disconnected at the coupling 32 from the first chamber 12, such as by disengaging the internal threads of the collar 35 from the flange 37 on the second chamber 26, and withdrawing the cannula 36.

With the second chamber 26 disconnected and separated from the first chamber 12, as indicated in FIG. 3f, the concentrated suspension of cells may be removed from the second chamber 26 such as by use of a syringe 41. If desired, the cells also may be maintained in the second chamber 26, such as for further processing. For example, the separated second chamber 26 with the desired cells may be placed in fluid communication with a further fluid destination or source, such as an additional chamber, for further treatment and concentration, as described below in reference to another example.

The example sedimentation assembly 10 may be used to reconstitute, wash, treat or concentrate a diverse set of cell preparations. For example, the biological material received by the first chamber 12 may be a relatively crude suspension of cells and may include individual cells, multi-cellular aggregates and/or cells associated with non-cellular material.

The suspension of cells may include one or more cell types. The suspension of cells also may include stem cells alone or in combination with other cell types, including other types of stem cells.

The sedimentation assembly 10 also may be used with cell preparations that have been subjected to purification procedures. For example, the sedimentation assembly 10 may be linked, connected to or otherwise incorporated into a system for purifying cells. In such an arrangement, the first chamber 12 of the sedimentation assembly 10 may receive a suspension of cells from the cell purification system. For instance, the suspension of cells received by the first chamber may be stem cells that have been isolated according to the presence or absence of a selected cell marker using affinity techniques. The suspension of cells may have been, for example, isolated as being CD34 positive.

As indicated, centrifugation may be used to produce a sedimentation force field to flow a suspension of cells from the first chamber 12 to the second chamber 26. When centrifugation is used, the sedimentation assembly 10 may be placed in a holder, for convenient further placement of the assembly in a centrifuge. The holder also may assist in stabilizing the assembly during centrifugation. The size and shape of the holder may be adapted to a given sedimentation assembly and centrifuge bucket. Such a holder also may be used to hold a sedimentation assembly for sedimentation at normal gravity force.

Figure 4:
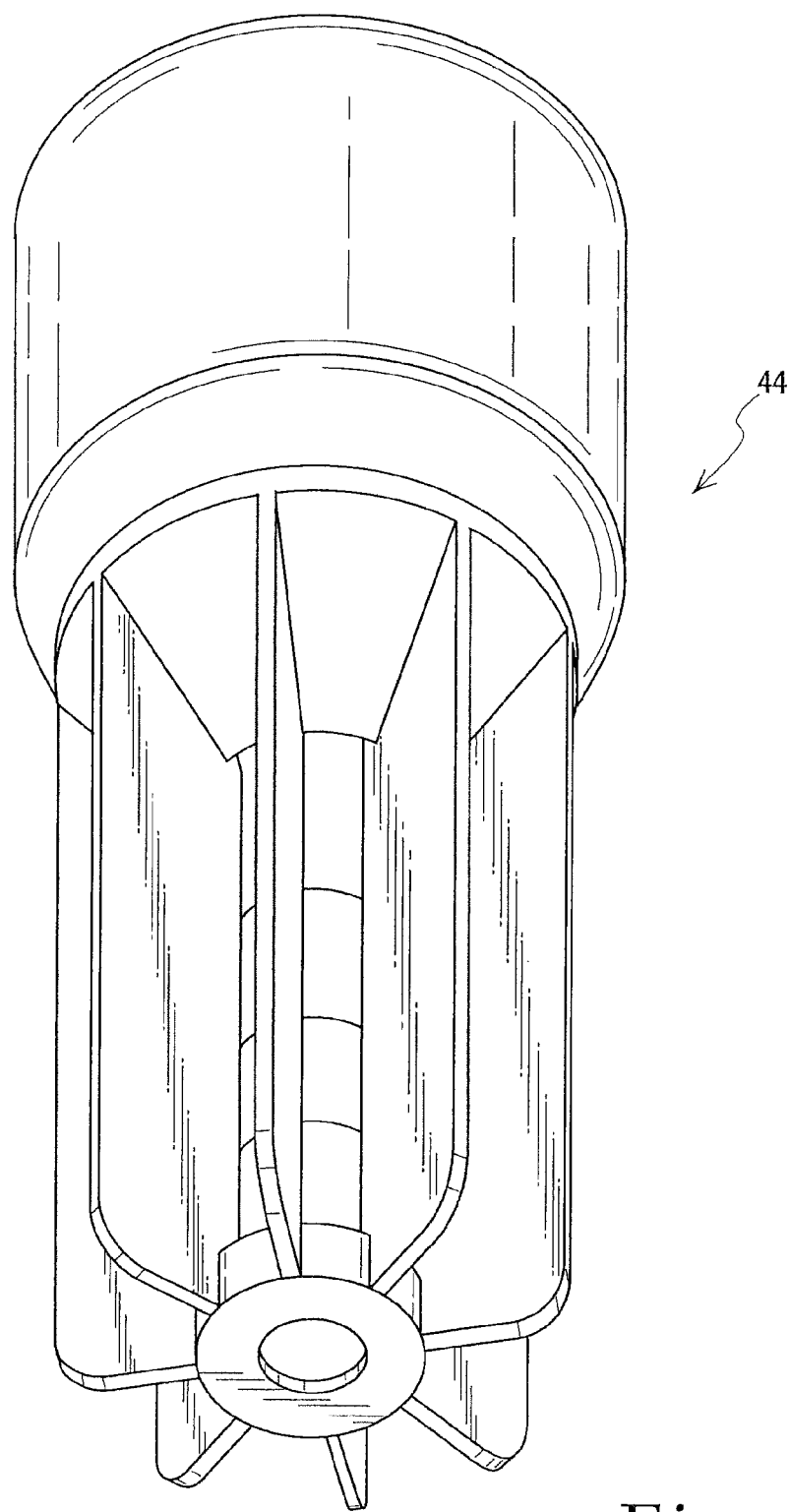
FIG. 4 is a perspective view of one example of a holder, holding a modified sedimentation assembly for use in a sedimentation force field, specifically generated by a centrifuge.
Figure 5:
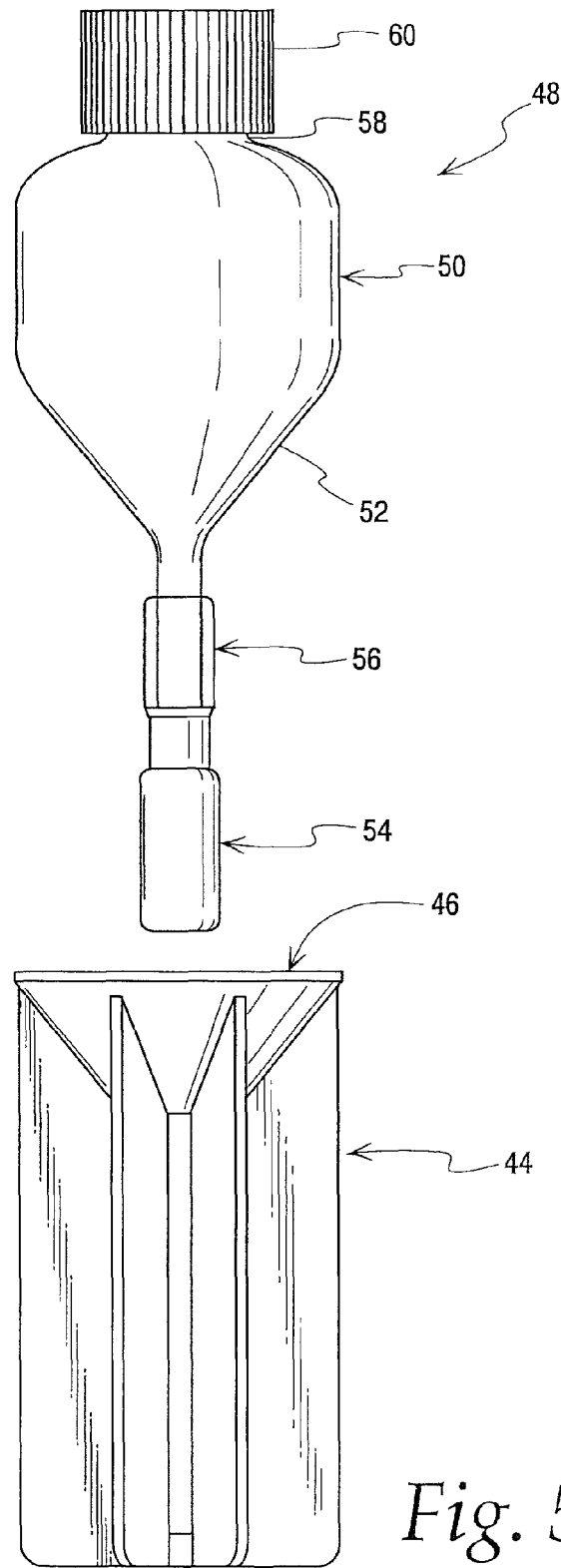
FIG. 5 shows a further example of a sedimentation assembly with a holder, such as the holder of FIG. 4.
Figure 6:
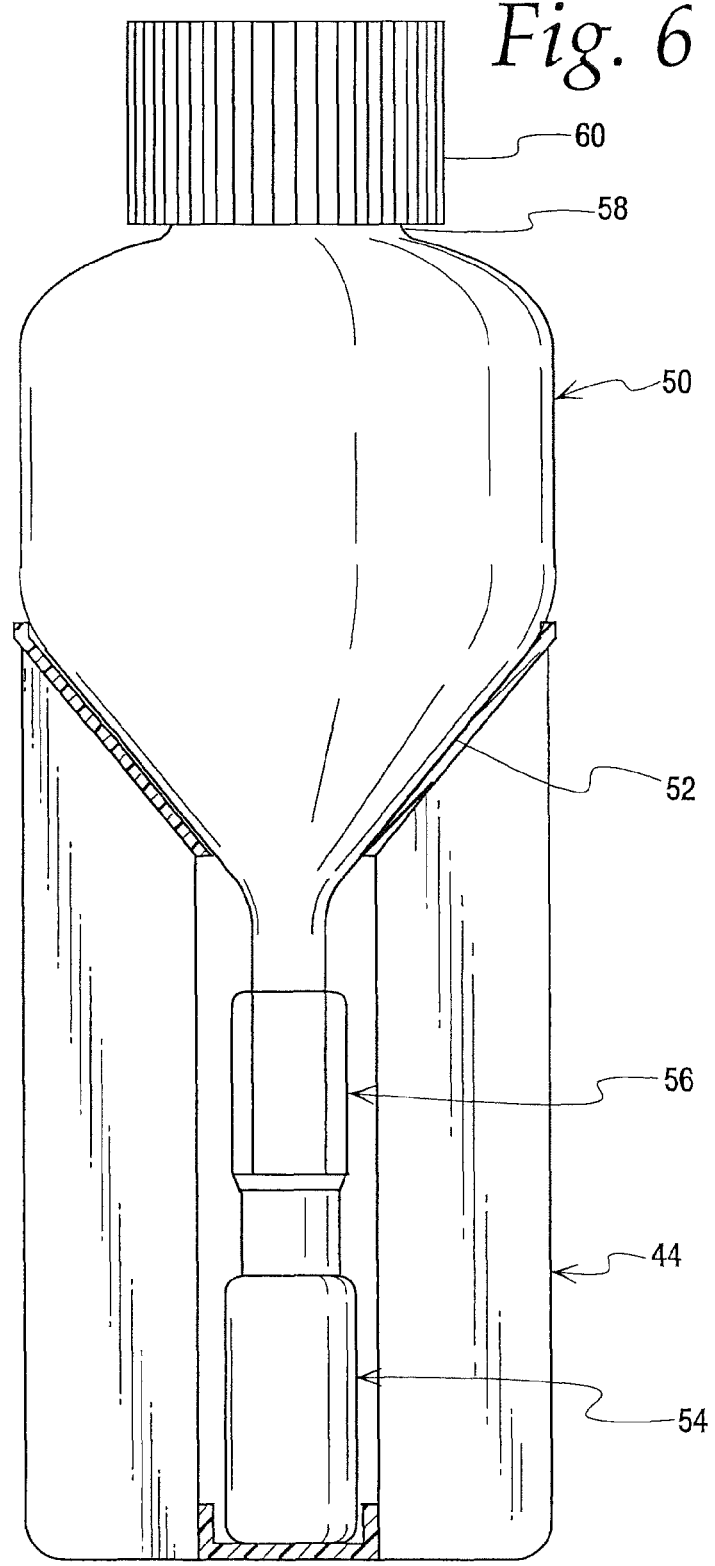
FIG. 6 is a cross-sectional view of the example of the holder with the sedimentation assembly of FIG. 4 located in the holder.

FIGS. 4-6 show an example of a holder 44 that may be used with a further example of a sedimentation assembly 48. FIG. 4 shows the example of a holder 44 that may be used to hold a sedimentation assembly 48 in a centrifuge bucket during centrifugation. The holder includes an opening 46, best seen in FIG. 5, for placement of the sedimentation assembly into the holder 44. In this example, the overall shape of the holder generally is cylindrical, to fit the most common shape of centrifuge buckets.

FIG. 5 shows the placement of the sedimentation assembly 48 into the holder 44 of FIG. 4. As shown, the sedimentation assembly includes a first chamber 50 with a concentration zone, 52 a second chamber 54, and a coupling 56. In this example, the first chamber 50 includes an inlet 58 for receiving a suspension of cells. The inlet 58 may be covered, for example, with a screw cap 60.

In FIG. 6, the sedimentation assembly 48 is shown placed within the holder 44, shown in cross-section, for use in a sedimenting procedure, as would occur during centrifugation. During the sedimenting procedure, the desired cells, initially in the first chamber 50, will become concentrated within the concentration zone 52, and will tend to flow into the second chamber 54, via the coupling 56.

FIGS. 7a-7g exemplify a use of a sedimentation assembly 61 according to the disclosure for performing multiple washing and/or treating steps of a cell population. The sedimentation assembly 61 includes a first chamber 64 and a second chamber 26. In FIG. 7a, the second chamber 26 contains a suspension of cells 62 that may require further processing. The suspension of cells in the second chamber 26 may result from processing according to previously described examples for obtaining a concentrated cell population such as is discussed, for example, with respect to use of the first chamber 12 in FIGS. 3a-3f.

As shown in FIG. 7b, the second chamber 26 with the suspension of cells 62 may be placed in fluid communication with another fluid destination or source, such as an additional first chamber 64 which may contain a washing or treatment solution. The connection of the two chambers may be facilitated by the presence of a coupling, such as previously discussed coupling 32 that allows for repeated coupling (in fluid communication) and uncoupling (not in fluid communication) of the chambers. The cells 62 then may flow into the additional first chamber 64, with the flow being enhanced simply by applying manual force to a wall of the second chamber 26, such as by squeezing the second chamber 26 while the sedimentation assembly 61 is in an inverted position. It will be appreciated that a sedimentation force field, such as a centrifugal force field, also may be applied to the inverted sedimentation assembly so as to facilitate the flow of cells from the second chamber 26 to the first chamber 64.

In examples where the cells are to be washed, the suspension of cells may be flowed from the second chamber 26 to an additional first chamber 64 that contains a large volume of a wash solution. In other examples, the cells may be flowed into an additional first chamber containing a relatively small volume of fluid, as might occur when the cells are to be treated with an expensive reagent. After flowing the cells from the second chamber 26 to the additional first chamber 64, to limit cell loss the second chamber 26 may remain connected with the first chamber 64, or alternatively may be disconnected from the first chamber 64.

After washing or treatment of the cells within the additional first chamber 64, the cells may be flowed back into the second chamber 26, which remains attached to the additional first chamber thereby allowing complete recovery of all the cells or at least reducing cell loss. This may be accomplished using a sedimentation force field, such as shown in FIG. 7c. Alternatively, the additional first chamber 64 may be connected to and placed in fluid communication with a new second chamber. The second chamber 26 then may be separated from the additional first chamber 64, resulting in a suspension of cells in the second chamber 26 that has been washed and re-concentrated, as seen in FIG. 7d.

If desired, the washed suspension of cells in the further second chamber 26 then may be flowed to yet another first chamber 68 for further processing, such as by additional washing or treatment. The connection and flowing of the suspension of cells from the second chamber 26 to the additional first chamber 68 is represented in FIG. 7e and is accomplished in a similar manner as with respect to the above description of FIG. 7b. As shown in FIG. 7f, the cells then may be flowed back to the original second chamber 26 or a new second chamber, such as by use of a sedimentation force field. The first and second chambers may remain attached and the use of the same second chamber may reduce cell loss. In this way, a suspension of cells may be repeatedly moved between "first" and "second" chambers that are placed in fluid communication, providing for repeated washing, treatment and/or re-concentration of the cells, shown deposited in the second chamber 26 in FIG. 7g.

FIGS. 8a-8h shows a further example of a sedimentation assembly 70 and a method of use thereof in accordance with the disclosure. The sedimentation assembly 70 includes a first chamber 72 for receiving a cell suspension and a second chamber 76, which can be in the form of a syringe. A coupling 78 can be used to place the chambers 72, 76 in fluid communication. As described with respect to the other examples, the second chamber 76 may be placed in fluid communication with a first chamber 72. The sedimentation assembly 70 with the first chamber 72 connected to the second chamber 76 may be placed in a sedimentation force field, such as shown in FIG. 8b, to flow a cell population 74 into the second chamber 76.

The flow of the cell population 74 to the second chamber 76, in the form of a syringe, also may be facilitated or accomplished by moving a piston 80 of the syringe 76, so as to create a vacuum in the second chamber 76, as shown by the displacement of the piston 80 in FIGS. 8c and 8d. This movement of the piston 80 causes fluid to be drawn into the second chamber 76 from the first chamber 72 to relieve the vacuum. The volume of the syringe chamber may be configured as fixed or variable, depending on anticipated fluid volume. In one example, retraction of the piston 80 will draw fluid into the second chamber thereby helping to recover cells that remain in the first chamber 72 or in the area of the coupling 78 even after the application of a sedimentation force field. In addition, retraction of the piston may be used to increase the amount of fluid in the second chamber, if desired. The piston 80 of the syringe 76 also may be pushed after the cell population has been flowed into the syringe 76, thereby removing excess supernatant from the second chamber and adjusting the volume in which the cells are suspended in the second chamber 76.

The second chamber 76 then may be removed from fluid communication with the first chamber 72, as illustrated in FIG. 8e. Given that the second chamber 76 is in the form of a syringe, the second chamber 76 may be used to administer the cells to a patient or used for other purposes. As indicated in FIG. 8f, the syringe also may be placed in fluid communication with a further fluid destination or source, such as a further first chamber 82, for further washing or treatment. The cells 74 may be flowed into the further first chamber 82 by movement of the piston 80 of the second chamber syringe 76, as shown in FIGS. 8f and 8g, or by application of a sedimentation force field, such as described above in reference to FIG. 8b. The cells also may be flowed back into the second chamber 76 (or into a further "second" chamber) to result in a concentrated cell population in the second chamber 76, as shown in FIG. 8h.

Figure 9:
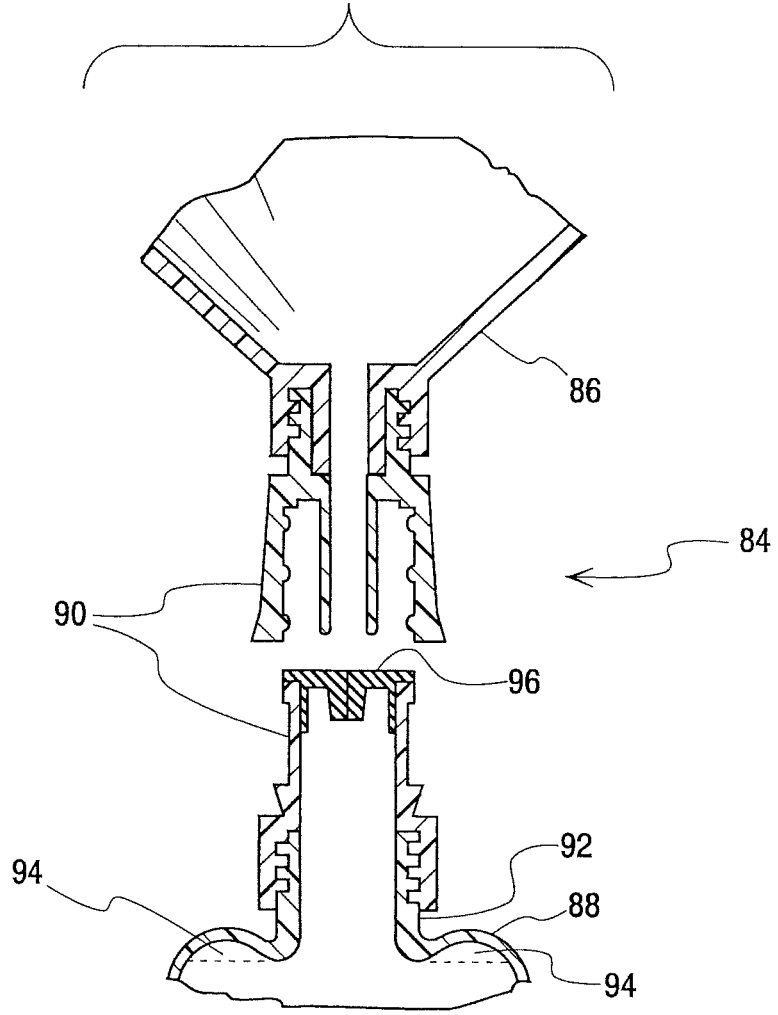
FIG. 9 is a cross-sectional view of a further example of a sedimentation assembly according to the disclosure.

A further example of a sedimentation assembly according to the disclosure is shown in FIG. 9. According to this example, one or both chambers of the sedimentation assembly is adapted by the provision of one or more air pockets to more easily allow the trapping of air in the chamber. This feature is beneficial when it is necessary to easily compress the contents of a chamber, such as occurs, for example, when a a structure such as needle or cannula must be introduced into a chamber filled with liquid.

The sedimentation assembly 84 shown in FIG. 9 is substantially similar to the example shown in FIGS. 1 and 2. That is, the sedimentation assembly 84 includes a first chamber 86, a second chamber 88, and a coupling 90. The coupling 90 shown in FIG. 9 is identical to that shown in FIG. 1a. In FIG. 9, the wall of the second chamber 88 curves upwards on both sides of inlet port 92, forming air-trapping pockets or regions 94 within the second chamber 88.

According to the example of FIG. 9, air is trapped in the air-trapping regions 94 when the chamber is placed upright and filled with liquid. When a syringe needle or similar device is inserted into the second chamber 88 through, for example, the septum 96, liquid is forced into the air-trapping regions because the trapped air is compressible, allowing a structure such as needle or cannula to more easily penetrate the chamber.

Further, other types of valves and couplings may be used with the sedimentation assembly of the disclosure. Resealable valves are preferred (and particularly preferably automatically resealable) to regulate the flow of fluid between the chambers, either alone or in combination with other valves. For example, stopcock valves as well as clamps are examples of manually resealable elements that may be used. In one example, a syringe-type needle may be used with a rubber plug forming a valve.

Other valves and couplings that may be used are disclosed, for example, in U.S. Pat. Nos. 4,683,916, 5,188,620, 5,957,898, 6,039,302 6,261,282 and 6,605,076 which are herein incorporated by reference in their entirety. These valves and others may employ a variety of septums and septum opening mechanisms, and may be employed with various types and shapes of coupling members such as needles, Luer members, cannulas, nozzles and hybrid structures.

FIG. 10a-d shows examples of such valves and connectors. In FIG. 10a, valve 100 has a resealable pre-slit septum 102 mounted on the first end 104 of a housing 106. The septum is mounted between annular, U-shaped, swaged end members 108 and an internal septum supporting ridge 110. As described more fully in U.S. Pat. Nos. 5,188,620 and 6,605,076, this septum is co-operative with a blunt cannula that may be inserted through septum slit 102 for introducing fluid into and through the valve.

A further example of a valve connector 200 is shown in FIG. 10b. In this example, a nozzle 202 in the form of a male Luer fitting is shown partially inserted into the valve 200 to establish a fluid flow path. Briefly, the insertion of the nozzle 202 depresses a gland or elastomeric member 204 and axially displaces a hollow internal post 206 to open a fluid flow path through the gland and the hollow post to valve outlet 208.

FIG. 10c shows a further example of a valve connector that may be used with an apparatus according to the disclosure. The valve connector 300 includes a resealable valve member 302 having an upper portion 304, middle portion 306 and annular skirt (not shown). One valve slit 308, extends downwardly through the upper portion 304 and middle portion 306 into a chamber 310. Engagement of a cannula against the face of the valve 302 causes the slit 314 to open and provides a fluid flow path through the slit and chamber 310 to the valve outlet.

FIG. 10d shows one further valve that may be used with the present apparatus. Specifically, the valve body 400 of FIG. 10d includes a male Luer portion 402 and a female Luer portion 404. A valve disc 406 is located within the valve body and rests on a triangular projection 408. The inherent resiliency of the valve disc normally biases it in a closed position as shown in solid lines. A valve actuator 410 is located in the female Luer bore, so that the insertion of a connecting male Luer forces the actuator 410 axially to engage and bend the edges of the valve disc 406 downwardly to an open position. The disc reseals upon removal of the connecting male Luer.

It will be understood that the examples provided in the present disclosure are illustrative of some of the applications of the principles of the present disclosure. Numerous modifications may be made by those skilled in the art without departing from the true spirit and scope of the disclosure. Various features which are described herein can be used in any combination and are not limited to particular combinations that are specifically described herein.

The invention claimed is:

1. An apparatus for concentrating cells in a suspension, the apparatus comprising:
   a first chamber for receiving a suspension including a cell population, the first chamber defined by a first container, said first chamber including a cell concentration zone, said concentration zone configured to receive a concentrated cell population; and a second chamber in fluid communication with the first chamber, the second chamber defined by a second container that is physically separable from the first chamber, the second chamber including:

(i) a housing defining the second chamber as a substantially spherical inner chamber with a substantially spherical inner chamber surface;
(ii) a port in said housing communicating with the inner chamber and configured to communicate with the first chamber;
(iii) the port including a resealable closure; and
(iv) the chamber having a cell-receiving pocket positioned generally opposite said port, the cell-receiving pocket depending outwardly from the substantially spherical inner chamber surface,
said first and second chambers configured to be placed together, as a unit, in a centrifugal force field, wherein upon application of the centrifugal force field said cell-receiving pocket is configured to receive at least a portion of the concentrated cell population from the cell concentration zone of the first chamber.

2. The apparatus of claim 1 further comprising a gas collection region defined by the second chamber.

3. The apparatus of claim 2 wherein said gas collection region is adjacent to said port.

4. The apparatus of claim 1 wherein said housing is compressible.

5. The apparatus of claim 1 wherein said resealable closure is selected from the group consisting of a septum, a pre-slit septum, an elastomeric member, a gland-type valve and combinations thereof.

6. An apparatus for receiving cells in a suspension, the apparatus comprising:
a first chamber for receiving a suspension including a cell population, the first chamber defined by a first container, said first chamber including a cell concentration zone, said concentration zone configured to receive a concentrated cell population; and a second chamber in fluid communication with the first chamber, the second chamber defined by a second container that is physically separable from the first chamber, the second chamber including:
(i) a housing defining second chamber as being a substantially spherical inner chamber;
(ii) a port in the housing communicating with the inner chamber and configured to communicate with the first chamber;
(iii) the port being the only opening in the housing and including a resealable closure;
(iv) the inner chamber including a defined gas collection region comprising a volume that is located higher than a lower end of the port when the port is positioned at a top of the chamber,
said first and second chambers configured to be placed together, as a unit, in a centrifugal force field, wherein upon application of the centrifugal force field said second chamber is configured to receive at least a portion of the concentrated cell population from the cell concentration zone of the first chamber.

7. The apparatus of claim 6 wherein the housing is compressible.

8. The apparatus of claim 6 wherein the gas collection region comprises a volume that is located higher than substantially the remainder of the chamber when the port is positioned at a top of the chamber.

9. The apparatus of claim 6 wherein the gas collection region comprises at least one pocket defined in an inner surface of the chamber.

10. The apparatus of claim 6 wherein the gas collection comprises at least one pocket defined in an inner surface of the chamber and the pocket is located higher than the substantially remainder of the chamber when the port is positioned at the top of the chamber.

11. The apparatus of claim 6 in which the resealable closure is selected from the group consisting of a septum, a pre-slit septum, an elastomeric member, a gland-type valve and combinations thereof.

12. An apparatus for receiving cells in a suspension, the apparatus comprising:
a first chamber for receiving a suspension including a cell population, the first chamber defined by a first container, said first chamber including a cell concentration zone, said concentration zone configured to receive a concentrated cell population; and a second chamber in fluid communication with the first chamber, the second chamber defined by a second container that is physically separable from the first chamber, the second chamber including:
(i) a housing defining the second chamber as being an inner chamber having an inner chamber surface;
(ii) a port being the only opening in the housing communicating with the inner chamber and configured to communicate with the first chamber;
(iii) a defined cell collection region in the inner chamber surface positioned generally opposite the port, the cell collection region depending outwardly from the inner chamber surface; and
(iv) a defined gas collection region on the inner chamber surface, the gas collection region comprising a volume that is located higher than a lower end of the port when the port is positioned at a top of the chamber,
said first and second chambers configured to be placed together, as a unit, in a centrifugal force field, wherein upon application of the centrifugal force field said cell collection region is configured to receive at least a portion of the concentrated cell population from the cell concentration zone of the first chamber.

13. The apparatus of claim 12 in which the housing is compressible.

14. The apparatus of claim 12 in which the port includes a resealable closure.

15. The apparatus of claim 12 in which the chamber is generally spherical.

16. The apparatus of claim 14 in which the resealable closure is selected from the group consisting of a septum, a pre-slit septum, an elastomeric member, a gland-type valve and combinations thereof.

* * * * *

UNITED STATES PATENT AND TRADEMARK OFFICE
CERTIFICATE OF CORRECTION

Page 1 of 1

PATENT NO. : 9,176,038 B2
APPLICATION NO. : 13/611211
DATED : November 3, 2015
INVENTOR(S) : Kyungyoon Min et al.

It is certified that error appears in the above-identified patent and that said Letters Patent is hereby corrected as shown below:

On the Title Page:

At Column 1, below Item (54), insert Item -- (71) Applicants: BAXALTA INCORPORATED, Bannockburn, IL (US); BAXALTA GMBH, Glattpark (Opfikon) (CH) --.

At Item (75), "(75)" should be -- (72) --.

Signed and Sealed this
Twenty-ninth Day of March, 2016

Michelle K. Lee
*Director of the United States Patent and Trademark Office*